United States Patent
Besson

(10) Patent No.: US 6,324,247 B1
(45) Date of Patent: Nov. 27, 2001

(54) PARTIAL SCAN WEIGHTING FOR MULTISLICE CT IMAGING WITH ARBITRARY PITCH

(75) Inventor: Guy M. Besson, Wauwatosa, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/475,835

(22) Filed: Dec. 30, 1999

(51) Int. Cl.$^7$ .................................................. A61B 6/03
(52) U.S. Cl. .............................. 378/15; 378/901
(58) Field of Search .................... 378/4, 15, 901

(56) References Cited

U.S. PATENT DOCUMENTS

| | | | |
|---|---|---|---|
| 5,606,585 | * | 2/1997 | Hu ........................................... 378/15 |
| 6,118,841 | * | 9/2000 | Lai ........................................... 378/19 |

OTHER PUBLICATIONS

"Optimal short scan convolution reconstruction for fanbeam CT", Dennis L. Parker, Med. Phys. 9(2), Mar./Apr. 1982.
"Optimization of short scan convolution reconstruction in fan beam CT, " Dennis L. Parker, IEEE 1982.
"A general approach to the reconstruction of x–ray helical computed tomography," Jiang Hsieh, Med. Phys. 23(2), Feb. 1996.
"New classes of helical weighting algorithms with applications to fast CT reconstruction," Guy Besson, Med. Phys. 25(8), Aug. 1998.
"An Optimized Reconstruction Algorithm for Temporal Resolution Improvement in CT Fluoroscopy," Jiang Hsieh, 1998.

* cited by examiner

*Primary Examiner*—David V. Bruce
(74) *Attorney, Agent, or Firm*—Armstrong Teasdale, LLP; Christian G. Cabou

(57) ABSTRACT

A method is provided for reconstructing an image from a set of projection data acquired in a computed tomgraphic (CT) scan of an object. The method includes selecting a pitch in a range between a zero pitch and a high-speed (HS) pitch, helically scanning the object with a CT imaging system having a multislice detector and a moving radiation source, at the selected pitch, to acquire projection data, and helically interpolating the acquired projection data to generate or synthesize projections in a plane of reconstruction for a source angle $\beta$ spanning a partial scan angle. The method also includes applying a partial scan weight $W_{PS}$ to the generated or synthesized projections in a plane of reconstruction, and filtering and backprojecting the weighted projections.

24 Claims, 4 Drawing Sheets

PARTIAL SCAN WEIGHTING FOR MULTISLICE CT IMAGING WITH ARBITRARY PITCH

BACKGROUND OF THE INVENTION

This invention relates generally to computed tomography (CT) imaging methods and apparatus, and more particularly to methods and apparatus for reconstructing images of objects from partial scans.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Ideally, in cardiac CT reconstruction, scanner speed would be matched to a heart rate of a patient so that as many contiguous (or slightly overlapped) sectors would be acquired as there are measuring rows in the imaging system. For a four-slice system, it is desirable to subdivide a range of source angles into four sectors that, when combined together, allow image reconstruction from data essentially acquired at the same cardiac phase. Although a minimum source angle span of 180+fan-angle ($\pi+2\Gamma$) is sought for reasons of adequate temporal resolution, it is not always possible to achieve this minimum due to the limited number of scanner speeds and wide range of patient heart rates. It would therefore be desirable to provide means and apparatus to provide image quality optimization for a given time resolution with full utilization of patient dose.

Due to the continuous range of patient cardiac motion, and the fixed number of scanner rotation speeds, cardiac sector reconstruction, in practice, leads to a usable data set that encompass more views than a minimum number required for half-scan reconstruction. Patient dose and image noise considerations indicate that it would be desirable to provide means and apparatus for a partial scan reconstruction in which any helical pitch faster than a high-quality (HQ) mode could be directly reconstructed.

BRIEF SUMMARY OF THE INVENTION

There is therefore provided, in one embodiment, a method for reconstructing an image from a set of projection data acquired in a computed tomographic (CT) scan of an object. The method includes the steps of: selecting a pitch in a range between a zero pitch and a high-speed (HS) pitch; helically scanning the object with a CT imaging system having a multislice detector and a moving radiation source, at the selected pitch, to acquire projection data; helically interpolating the acquired projection data; to generate or synthesize projections in a plane of reconstruction for a source angle $\beta$ spanning a partial scan angle; applying a partial scan weight $W_{PS}$ written as:

$$W_{PS}(\beta, \gamma) = \frac{\beta - \frac{\pi}{2} + \Gamma}{2(\Gamma - \gamma)} \quad \beta_{inf} = \frac{\pi}{2} - \Gamma \le \beta \le \beta^- = \frac{\pi}{2} + \Gamma - 2\gamma \quad (1)$$

$$W_{PS}(\beta, \gamma) = 1.0 \quad \beta^- \le \beta \le \beta^+ = 3\frac{\pi}{2} - \Gamma - 2\gamma$$

$$W_{PS}(\beta, \gamma) = \frac{3\frac{\pi}{2} + \Gamma - \beta}{2(\Gamma + \gamma)} \quad \beta^+ \le \beta \le \beta_{sup} = 3\frac{\pi}{2} + \Gamma$$

to the generated or synthesized projections in a plane of reconstruction, where $\gamma$ is a fan angle, $\beta$ a source angle, and $\Gamma$ a maximum fan angle; and filtering and backprojecting the weighted projections.

The above described embodiment permits full utilization of patient dose in a scan, such as a cardiac scan with different pitches, while optimizing image quality for a given time resolution. Reconstruction can be accomplished from any set of projection data larger or equal to a minimum required for half-scan reconstruction, up to a full rotation. In addition, partial scan weighting enables any helical pitch faster than HQ mode to be directly reconstructed, thus allowing continuous pitch selection in a given interval (which may be geometry dependent).

DETAILED DESCRIPTION OF THE INVENTION

Figure 1:
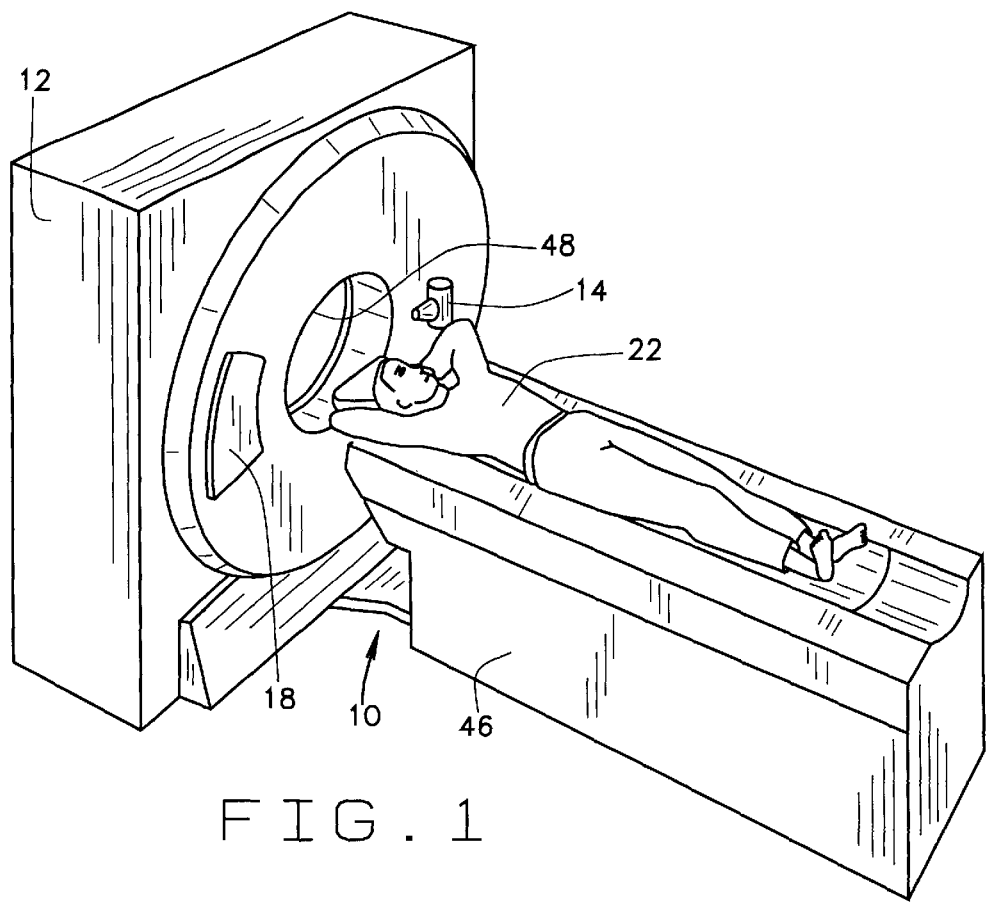
FIG. 1 is a pictorial view of a CT imaging system.
Figure 2:
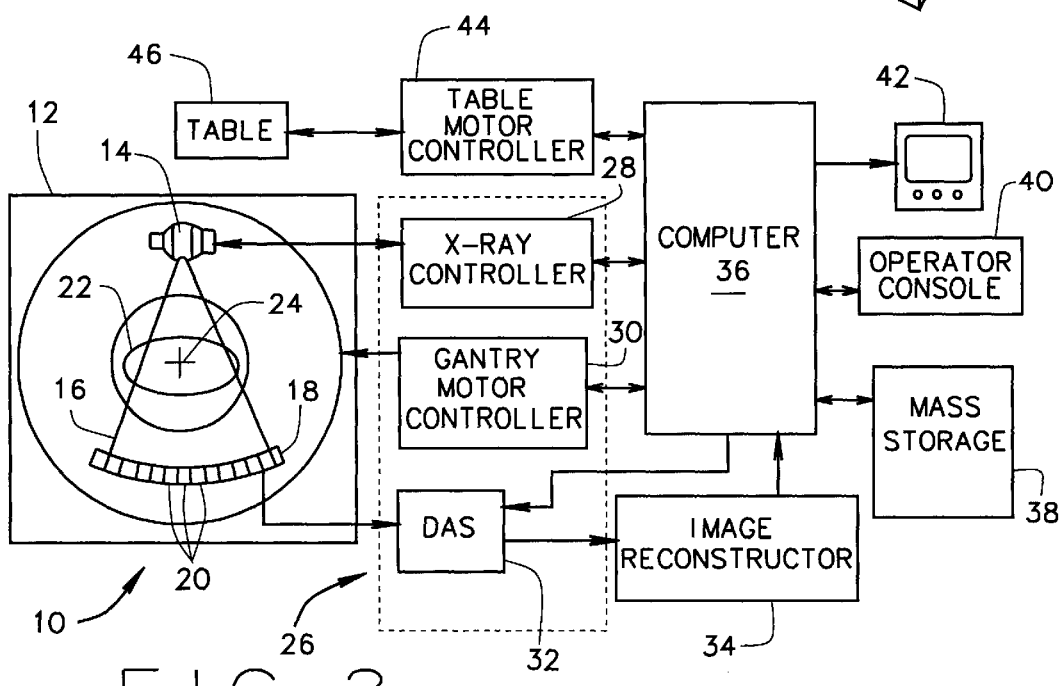
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
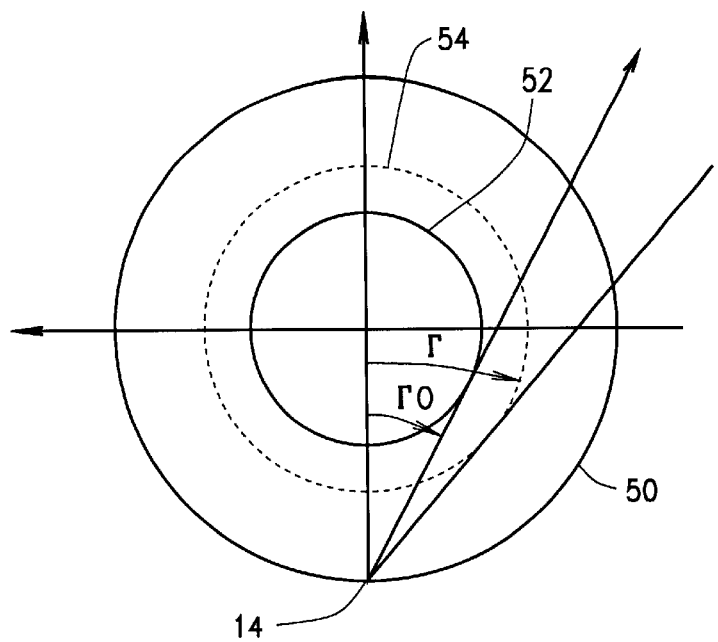
FIG. 3 is a representation of a scanning geometry of CT imaging system 10.

FIG. 3 is a representation of a scanning geometry of CT imaging system 10. During a scan, source 14 follows a trajectory indicated by outer circle 50. Object or patient 22 is located within a scan field of view (SFOV) delimited by circle 52. Fan angle $\Gamma$ is a maximum fan angle, where $\Gamma=\pi/2$ would correspond to SFOV circle 52 being superimposed on source trajectory 50. In one embodiment of the present invention, half-scan (segment) weights are transformed into partial scan or helical weights for any set of projections comprising source data for a source angle span in $[\pi+2\Gamma, 2\pi]$. In this source angle span, $\pi+2\Gamma$ is a minimum data set required to reconstruct an entire Scan Field Of View (SFOV), and $2\pi$ reduces to a known (for single-slice) helical algorithm. The method described below introduces a new multi-slice partial scan axial or helical algorithm for any source angle span in an interval $[\pi+2\Gamma, 2\pi]$. A maximum fan-angle $\Gamma$ is taken as a variable varying from $\Gamma_0$ (as given by the geometry for a given scanner) to $\pi/2$ for the purpose of deriving weights used in this embodiment of the present invention. Dashed circle 54 delimits a representative SFOV for an arbitrary $\Gamma$.

Considering a derivation of the half-scan formula, with $\Gamma$ being the maximum fan-angle, partial scan weights for part of the scan data acquired with the source angle $\beta$ in $[0, 2\pi]$ and centered on $\pi$ are written as:

$$W_{PS}(\beta, \gamma) = \frac{\beta - \frac{\pi}{2} + \Gamma}{2(\Gamma - \gamma)} \quad \beta_{inf} = \frac{\pi}{2} - \Gamma \le \beta \le \beta^- = \frac{\pi}{2} + \Gamma - 2\gamma \quad (1)$$

$$W_{PS}(\beta, \gamma) = 1.0 \quad \beta^- \le \beta \le \beta^+ = 3\frac{\pi}{2} - \Gamma - 2\gamma$$

$$W_{PS}(\beta, \gamma) = \frac{3\frac{\pi}{2} + \Gamma - \beta}{2(\Gamma + \gamma)} \quad \beta^+ \le \beta \le \beta_{sup} = 3\frac{\pi}{2} + \Gamma$$

In particular, by substituting $\Gamma=\Gamma_0$ in the equation above, and using a weight-smoothing transformation written as:

$$f(x) = 3x^2 - 2x^3 \quad (2)$$

with $$x = W_{PS}(\beta, \gamma)$$

one obtains half-scan weights centered on source angle $\beta=\pi$. The transformation f(x) is thus a smoothing function that can be used with any partial scan algorithm to smooth weights or the first derivative of the weights. Other smoothing functions are used in other embodiments.

Figure 4:
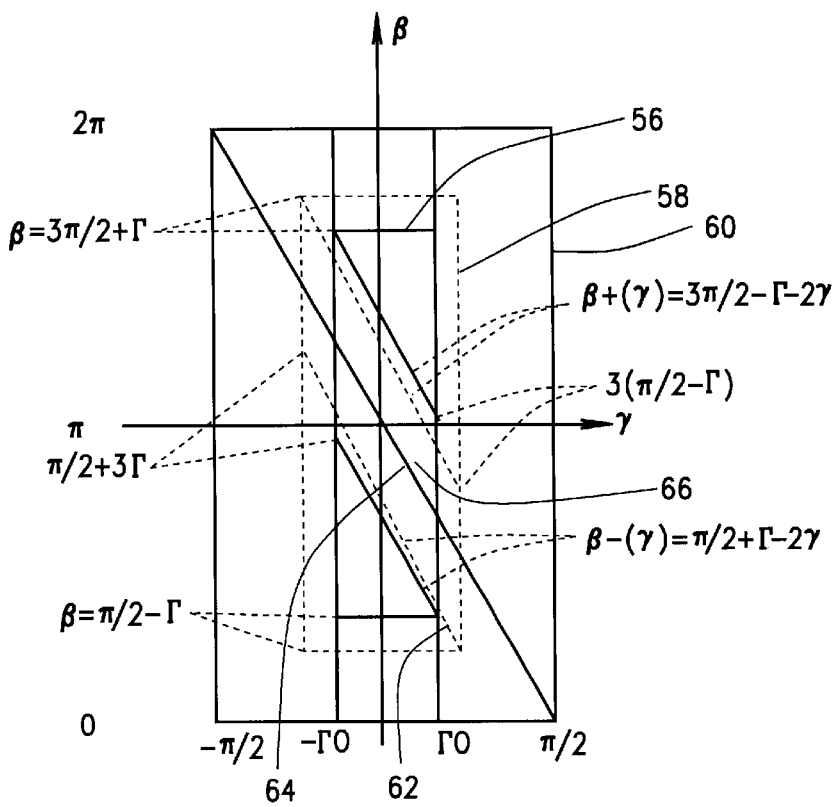
FIG. 4 is a representation of three sets of partial-scan weights.

In one embodiment of the invention, equation (1), with or without use of a transformation such as given by (2), also provides a partial scan weighting algorithm for any value of $\Gamma$ in $[\Gamma_0, \pi/2]$. FIG. 4 is a representation of projection data (a sinogram) for a source angle spanning $[0, 2\pi]$. Actual fan beam 16 data covers fan angles in a range $[-\Gamma_0, \Gamma_0]$. Data for points outside of this range of fan angles are taken as zero. Three sets of partial-scan weights are represented in FIG. 4. A first set represented by a solid inner rectangle 56 is for the case $\Gamma=\Gamma_0$. A second set of weight represented by dashed inner rectangle 58 is for $\Gamma$ in a range $]\Gamma_0, \pi/2[$. A third set of weights is represented by a solid outer rectangle 60 is for the case $\Gamma=\pi/2$. An area of weights equal to 1.0, represented by an interior of a parallelogram delimited by lines $\beta_{inf}=\pi/2-\Gamma$, $\beta_{sup}=3\pi/2+\Gamma$, $\beta-$ and $\beta+$ is seen to decrease from a first area 62 to a second area 64, where it is reduced to a single line described by $\beta=\pi-2\gamma$. When partial scan weights are described by equation (1), they lead to helical weights in region 64 as $$\Gamma \to \frac{\pi}{2}.$$

An intermediate case represented by area 66 defines a region of partial scan weights in one embodiment of the present invention.

Taking a limit as $\Gamma=\pi/2$, the following helical weights $W_{HI}(\beta, \gamma)$ are written:

$$W_{HI}(\beta, \gamma) = \frac{\beta}{\pi - 2\gamma}; 0 \le \beta \le \pi - 2\gamma \quad (3)$$

$$W_{HI}(\beta, \gamma) = \frac{2\pi - \beta}{\pi + 2\gamma}; \pi - 2\gamma \le \beta \le 2\pi$$

In one embodiment, equation (1) is used to reconstruct multislice helical data acquired at any selected pitch in a range between a high quality (HQ) pitch and a high-speed (HS) pitch. As used herein, an "HQ pitch" is a pitch in which it is possible for imaging system 10 to acquire at least two samples at different source positions for any projection ray through a plane to be reconstructed. An "HS pitch" is a pitch for imaging system 10 in which at least one sample for any projection ray through a plane to be reconstructed is acquired (the amount of data collected closely matches or equals that necessary to perform a half-scan reconstruction). For a typical imaging system 10, an "HS pitch" is one in which the amount of data collected to form a half scan reconstruction is 180° plus one fan angle of radiation beam 16. (A "fan angle" is an effective imaging angle of radiation beam 16 in an imaging plane. In a typical imaging system 10, a fan angle is equal to an angle of radiation beam 16 intercepted by a slice of detector 18 in a plane perpendicular to an axis of rotation of gantry 12. If the entire detector 18 is not used for image reconstruction, e.g., such as if radiation beam 16 is limited by collimation from striking the entire detector, the "fan angle" will, of course, be reduced. In this case, the minimum amount of data for reconstruction becomes less than $\pi+2\Gamma_0$.) In embodiments of imaging system 10 having more than one HQ pitch and/or HS pitch, the range referred to herein is bounded by the highest HQ pitch and the lowest HS pitch. For illustration, for one embodiment of a four-slice scanner, a corresponding pitch range is 3:1 to 6:1. For one embodiment of an eight-slice scanner, it is 7:1 to about 11:1. Higher HS modes (pitches) are possible with some data extrapolation. In other embodiments of an N-slice (or N-row) system, a corresponding pitch range from HQ to HS pitch is typically about N−1:1 to 2N:1, although other ranges are possible. In an embodiment intended for cardiac applications of imaging system 10, i.e., applications in which a heart of patient 22 is scanned, the invention is useful down to zero pitch.

In one embodiment, a pitch is selected in a range between an HQ pitch and an HS pitch. An object such as a patient 22 in FIG. 1 is helically scanned with a CT imaging system 10 having a multislice detector 18 and a moving radiation source 14. (The rotation of gantry 12 in FIG. 1 moves radiation source 14 and detector 18 on a helical trajectory around patient 22 as table 46 moves through gantry opening 48.) A helical interpolation is performed on the acquired projection data, such as by interpolating from row-to-row when only one source position is available for the ray considered, or by interpolating from row-to-row and with conjugate rays when a conjugate source position is available. This procedure generates or synthesizes projections in a plane of reconstruction for a source angle $\beta$ spanning a partial scan angle (for example, from 235 degrees to 360 degrees). Next, the partial scan weights of equation (1) are applied, and the image is reconstructed by filtering and backprojecting the weighted data. This embodiment is particularly useful in cardiac CT reconstruction, where it is not always possible to achieve a minimum source angle span of 180°+fan angle ($\pi+2\Gamma$) to achieve high temporal resolution with full utilization of patient dose. It is also particularly useful to provide the user with a "continuous pitch" in any given interval, such as [3,8] for a four-slice scanner or [7,16] for an eight-slice scanner.

Figure 5:
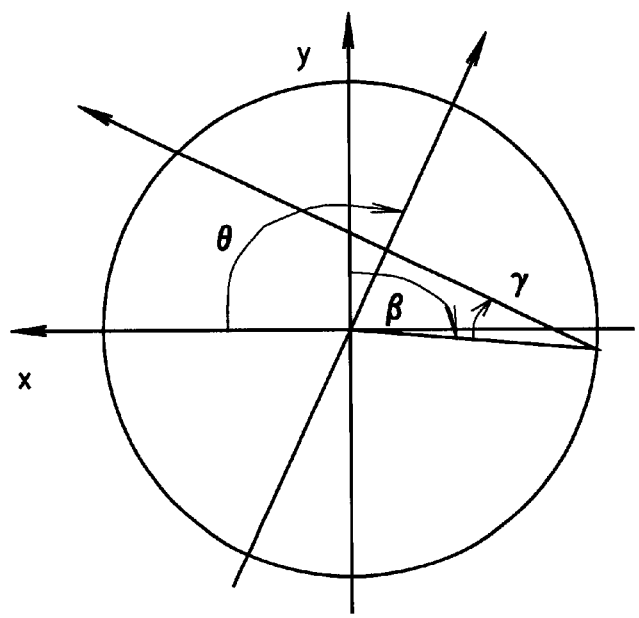
FIG. 5 is a diagram showing a relation between fan-beam and parallel coordinates.

A half-scan (for example, centered on $\pi$) where each ray is sampled exactly once is acquired when, in parallel projections, a parallel projection angle spans the interval $[\pi/2, 3\pi/2[$. FIG. 5 shows a relation between fan-beam and parallel coordinates. A parallel direction angle $\theta$ is given by $\theta=\beta+\gamma$ when $\theta=0$ is on the x-axis, $\beta=0$ is on the y-axis, and all angles are positive clockwise. A full data set for half scan reconstruction is acquired when $\theta$ varies between $\pi/2$ and $3\pi/2$.

Accordingly, weights for a half-scan are written as:

$$W_{PHS}(\theta) = 1.0; \frac{\pi}{2} \leq \theta \leq 3\frac{\pi}{2} \tag{4}$$

or equivalently:

$$W_{PHS}(\beta, \gamma) = 1.0; \frac{\pi}{2} - \gamma \leq \beta \leq 3\frac{\pi}{2} - \gamma. \tag{5}$$

Figure 6:
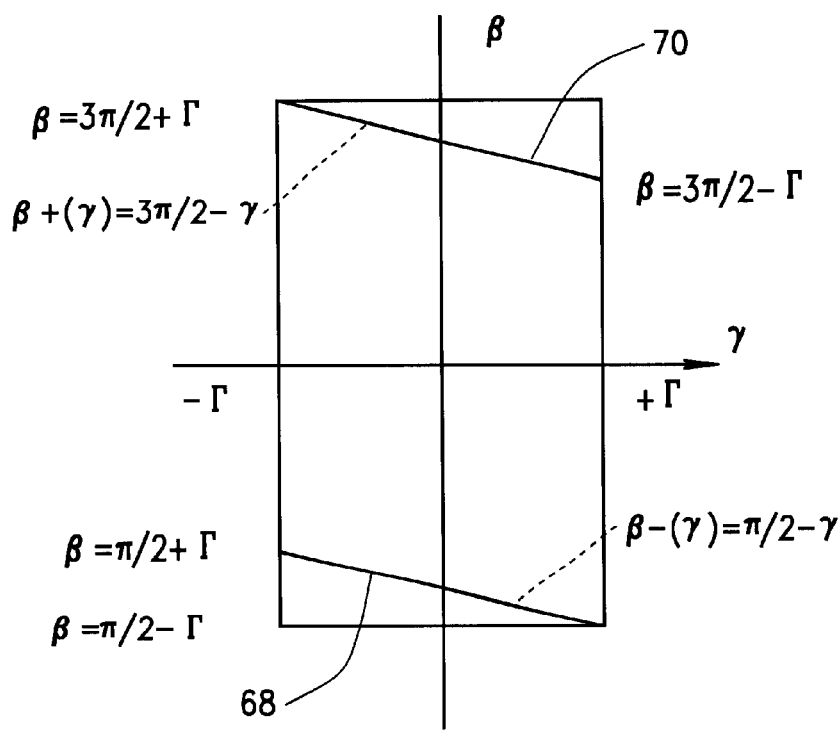
FIG. 6 is a representation of fan-beam scan weights derived directly from parallel projections.

A sinogram distribution of these weights is shown in FIG. 6, which shows a representation of fan-beam half-scan weights derived directly from parallel projections as in equation (4). Weights are 1.0 in an area delimited by lines 68 and 70, i.e., $\beta-(\gamma)$ and $\beta+(\gamma)$ respectively. For use in fan beam, these parallel weights are smoothed in one embodiment to achieve acceptable reconstructed image quality.

In one family of embodiments, a fan-beam helical reconstruction algorithm provides fan-beam helical reconstruction for any pitch between HQ and HS modes without patient dose waste or distortion of a slice sensitivity profile. A mathematical linkage between helical weighting $W_{HI}$ and "parallel projection" half-scan weighting $W_{PHS}$ is used to advantage. This linkage is illustrated by using a helical weighting obtained as a limit of the partial scan weights of equation (1) when $\Gamma=\pi/2$, cf. Equation (3). Weight $W_{HI}$ is then used as an input to a weight smoothing function $f_n$:

$$f_n(x)=f[f_{n-1}(x)]$$

where:

$$f(x)=3x^2-2x^3$$

From this, it follows that:

$$f_n(x) \xrightarrow[n\to\infty]{} 0; \quad 0 \leq x < 1/2;$$

$$f_n(x) \xrightarrow[n\to\infty]{} 1; \quad 1/2 < x \leq 1.$$

because f is continuous, $$0 \leq f(x) \leq 1 \text{ for } 0 \leq x \leq 1$$

and $$f(x) < x \text{ for } 0 < x < \frac{1}{2}$$

$$f(x) > x \text{ for } \frac{1}{2} < x < 1$$

Accordingly, it is written:

$$f_n[W_{HI}(\beta, \gamma)] \xrightarrow[n\to\infty]{} W_{PHS}(\beta, \gamma)$$

Each intermediate result $f_n$ therefore defines a helical weighting, because $W_{HI}$ is an helical weighting. Therefore, if $$w_1+w_2=1 \text{ with } 0 \leq w_1 \leq 1 \; 0 \leq w_2 \leq 1$$

then:

$$f(w_1)+f(w_2)=1 \tag{6}$$

and:

$$f_n(w_1)+f_n(w_2)=1, \forall n.$$

Figure 7:
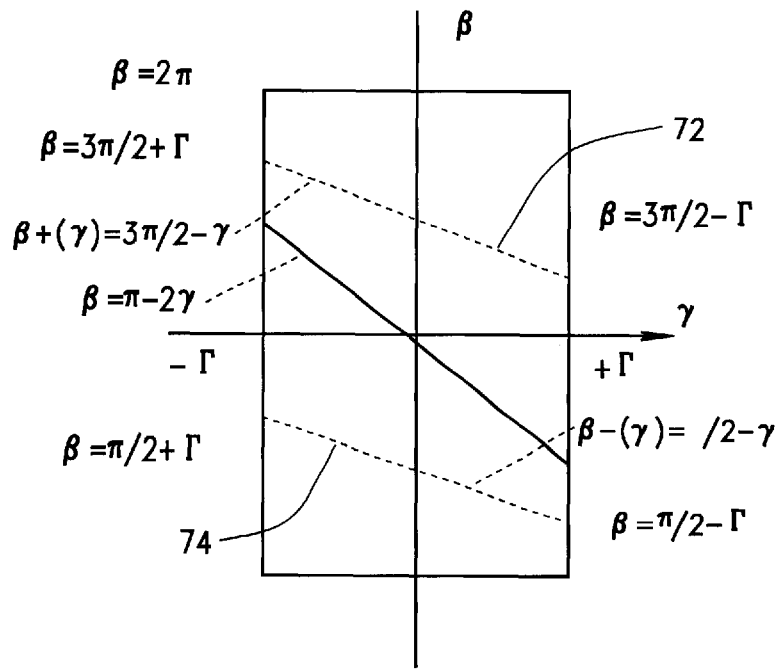
FIG. 7 is a representation of a limit relationship between helical weights and "parallel-half scan" weights.

Therefore, a helical weight normalization condition for any pair of conjugate rays is maintained, as shown in FIG. 7, which is an illustration of a limit relationship between helical weights and "parallel-half scan" weights. Lines 72 and 74 limit an area in which half scan weights are equal to 1.0. Lines 72 and 74 are lines in which helical weights $W_{HI}$ are equal to ½. Thus, in this family of embodiments, partial scan weights $W_{PS}$ are smoothed by a function $f_n$, for a selected value of n, $\infty \geq n \geq 0$, where $f_n(x)=f(f_{n-1}(x))$, $f(x)=f_1(x)=3x^2-2x^3$, and $f_0(x)=1$. Thus, there are embodiments in which n=1, n=2, n=3, etc. (There is also an embodiment in which n=0, in which case $f_n(x)=1$.)

Figure 8:
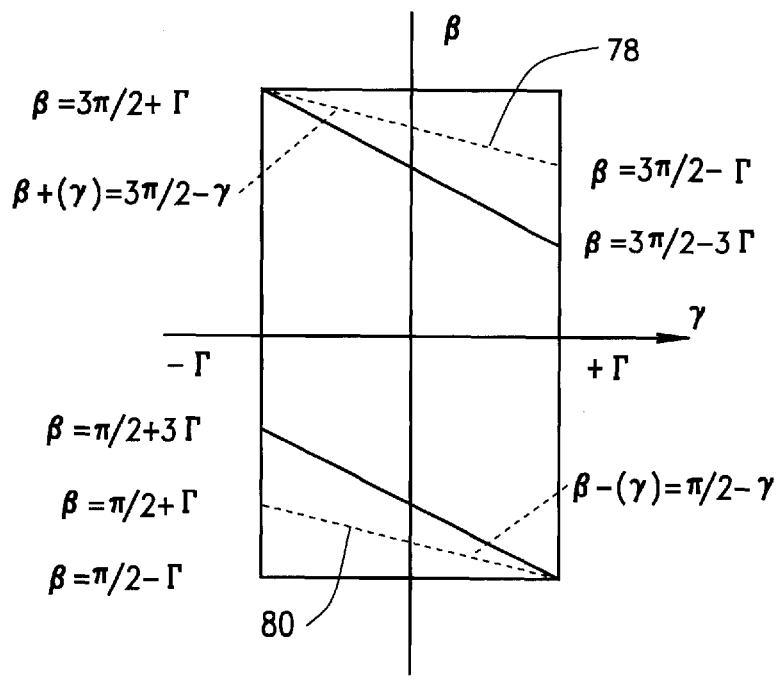
FIG. 8 is a representation of a limit relationship between half scan weights and parallel half scan weights.

In FIG. 8, a limit relation between half scan weights and "parallel half-scan" weights is illustrated by two dashed lines 78, 80 that limit an area of a sinogram where parallel half-scan weights are equal to 1.0 and that correspond to lines at which half-scan weights are equal to ½. Accordingly, application of f(x) to half-scan weights defines an infinite class of half-scan weights.

In other embodiments, other smoothing functions are available to define other helical, partial, and half-scan weightings. For instance, a function f(x) written as:

$$f(x) = \sin^2\left(\frac{\pi}{2}[x]\right); 0 \le x \le 1 \quad\quad 5$$

meets requirements expressed in (6) for limits used in determining weights of embodiments of the present invention. Thus, in one embodiment, partial scan weights $W_{PS}$ are smoothed using a function $f_n$, for a selected value of n, where $f_n$ is defined by a relationship written as $f_n = f(f_{n-1}(x))$; where f(x) is written:

$$f(x) = \sin^2\left(\frac{\pi}{2}[x]\right); 0 \le x \le 1.$$

Embodiments of the present invention are also applicable to cine or dynamic scans, in which table 46 remains stationary while gantry 12 rotates up to a plurality of times, and to CT fluoroscopy.

From the preceding description of various embodiments of the present invention, it is evident that the above described embodiments permit full utilization of patient dose in a CT image scanning while optimizing image quality for a given time resolution. Reconstruction is accomplished from any set of projection data larger or equal to a minimum required for half-scan reconstruction, up to a full rotation, and direct reconstruction is possible for any helical pitches faster than HQ mode.

Although particular embodiments of the invention have been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a fill-ring stationary detector and only the x-ray source rotates with the gantry, may be used if individual detector elements are corrected to provide substantially uniform responses to a given x-ray beam. Accordingly, the spirit and scope of the invention are to be limited only by the terms of the appended claims and legal equivalents.

What is claimed is:

1. A method for reconstructing an image from a set of projection data acquired in a computed tomographic (CT) scan of an object, comprising the steps of:

selecting a pitch in a range between a zero pitch and an HS pitch;

helically scanning the object with a CT imaging system having a multislice detector and a moving radiation source, at the selected pitch, to acquire projection data;

helically interpolating the acquired projection data to generate or synthesize projections in a plane of reconstruction for a source angle β spanning a partial scan angle;

applying a partial scan weight $W_{PS}$ written as:

$$W_{PS}(\beta, \gamma) = \frac{\beta - \frac{\pi}{2} + \Gamma}{2(\Gamma - \gamma)} \quad \beta_{inf} = \frac{\pi}{2} - \Gamma \le \beta \le \beta^- = \frac{\pi}{2} + \Gamma - 2\gamma \quad (1)$$

$$W_{PS}(\beta, \gamma) = 1.0 \quad \beta^- \le \beta \le \beta^+ = 3\frac{\pi}{2} - \Gamma - 2\gamma$$

$$W_{PS}(\beta, \gamma) = \frac{3\frac{\pi}{2} + \Gamma - \beta}{2(\Gamma + \gamma)} \quad \beta^+ \le \beta \le \beta_{sup} = 3\frac{\pi}{2} + \Gamma$$

to the generated or synthesized projections in a plane of reconstruction, where γ is a fan angle, β a source angle, and Γ a maximum fan angle; and filtering and backprojecting the weighted projections.

2. A method in accordance with claim 1 wherein the CT imaging system acquires four slices simultaneously, and the selected pitch is between 3:1 and 6:1.

3. A method in accordance with claim 1 wherein the CT imaging system acquires eight slices simultaneously, and the selected pitch is between 7:1 and 11:1.

4. A method in accordance with claim 1 wherein the CT imaging system acquires N slices and the selected pitch is between N−1:1 and 2N:1.

5. A method in accordance with claim 1 further comprising the step of smoothing partial scan weights $W_{PS}$ using a function $f_n$, for a selected value of n, where function $f_n$ is defined by a relationship written as $f_n(x) = f(f_{n-1}(x))$, $f(x) = f_1(x) = 3x^2 - 2x^3$, and $f_0(x) = 1$.

6. A method in accordance with claim 5 wherein the CT imaging system acquires four slices simultaneously, and the selected pitch is between 3:1 and 6:1.

7. A method in accordance with claim 5 wherein the CT imaging system acquires eight slices simultaneously, and the selected pitch is between 7:1 and 11:1.

8. A method in accordance with claim 5 wherein the CT imaging system acquires N slices and the selected pitch is between N−1:1 and 2N:1.

9. A method in accordance with claim 1 further comprising the step of smoothing partial scan weights $W_{PS}$ using a function $f_n$, for a selected value of n, where function $f_n$ is defined by a relationship written as $f_n(x) = f(f_{n-1}(x))$, $$f(x) = f_1(x) = \sin^2\left(\frac{\pi}{2}[x]\right); 0 \le x \le 1, \text{ and } f_0(x) = 1.$$

10. A method in accordance with claim 9 wherein the CT imaging system acquires four slices simultaneously, and the selected pitch is between 3:1 and 6:1.

11. A method in accordance with claim 9 wherein the CT imaging system acquires eight slices simultaneously, and the selected pitch is between 7:1 and 11:1.

12. A method in accordance with claim 9 wherein the CT imaging system acquires N slices and the selected pitch is between N−1:1 and 2N:1.

13. A computed tomography (CT) imaging system having a multislice detector and a moving radiation source, said imaging system configured to:

select a pitch in a range between a zero pitch and an HS pitch;

helically scan an object with a CT imaging system having a multislice detector and a moving radiation source, at the selected pitch, to acquire projection data;

helically interpolate the acquired projection data to generate or synthesize projections in a plane of reconstruction for a source angle β spanning a partial scan angle;

apply a partial scan weight $W_{PS}$ written as:

$$W_{PS}(\beta, \gamma) = \frac{\beta - \frac{\pi}{2} + \Gamma}{2(\Gamma - \gamma)} \quad \beta_{inf} = \frac{\pi}{2} - \Gamma \le \beta \le \beta^- = \frac{\pi}{2} + \Gamma - 2\gamma \quad (1)$$

-continued $$W_{PS}(\beta, \gamma) = 1.0 \qquad \beta^- \leq \beta \leq \beta^+ = 3\frac{\pi}{2} - \Gamma - 2\gamma$$

$$W_{PS}(\beta, \gamma) = \frac{3\frac{\pi}{2} + \Gamma - \beta}{2(\Gamma + \gamma)} \qquad \beta^+ \leq \beta \leq \beta_{sup} = 3\frac{\pi}{2} + \Gamma$$

to the generated or synthesized projections in a plane of reconstruction, where γ is a fan angle, β a source angle, and Γ a maximum fan angle; and filter and backprojecting the weighted projections.

14. A CT imaging system in accordance with claim 13 wherein the CT imaging system acquires four slices simultaneously, and the selected pitch is between 3:1 and 6:1.

15. A CT imaging system in accordance with claim 13 wherein the CT imaging system acquires eight slices simultaneously, and the selected pitch is between 7:1 and 11:1.

16. A CT imaging system in accordance with claim 13 wherein the CT imaging system acquires N slices and the selected pitch is between N–1:1 and 2N:1.

17. A CT imaging system in accordance with claim 13 further configured to smooth partial scan weights $W_{PS}$ using a function $f_n$, for a selected value of n, where function $f_n$ is defined by a relationship written as $f_n(x)=f(f_{n-1}(x))$, $f(x)=f_1(x)=3x^2-2x^3$, and $f_0(x)=1$.

18. A CT imaging system in accordance with claim 17 wherein the CT imaging system acquires four slices simultaneously, and the selected pitch is between 3:1 and 6:1.

19. A CT imaging system in accordance with claim 17 wherein the CT imaging system acquires eight slices simultaneously, and the selected pitch is between 7:1 and 11:1.

20. A CT imaging system in accordance with claim 17 wherein the CT imaging system acquires N slices and the selected pitch is between N–1:1 and 2N:1.

21. A CT imaging system in accordance with claim 13 further configured to smooth partial scan weights $W_{PS}$ using a function $f_n$, for a selected value of n, where function $f_n$ is defined by a relationship written as $f_n(x)=f(f_{n-1}(x))$, $$f(x) = f_1(x) = \sin^2\left(\frac{\pi}{2}[x]\right);\ 0 \leq x \leq 1,\ \text{and}\ f_0(x) = 1.$$

22. A CT imaging system in accordance with claim 21 wherein the CT imaging system acquires four slices simultaneously, and the selected pitch is between 3:1 and 6:1.

23. A CT imaging system in accordance with claim 21 wherein the CT imaging system acquires eight slices simultaneously, and the selected pitch is between 7:1 and 11:1.

24. A CT imaging system in accordance with claim 21 wherein the CT imaging system acquires N slices and the selected pitch is between N–1:1 and 2N:1.

* * * * *